US011672908B2

(12) United States Patent
Mason et al.

(10) Patent No.: US 11,672,908 B2
(45) Date of Patent: Jun. 13, 2023

(54) INTRAVENOUS FILTER

(71) Applicant: CareFusion 303, Inc., San Diego, CA (US)

(72) Inventors: Eugene Mason, La Habra Heights, CA (US); Jason Andrew Wine, Placentia, CA (US); Raymond P. Feith, Chino Hills, CA (US)

(73) Assignee: CareFusion 303, Inc., San Diego, CA (US)

( * ) Notice: Subject to any disclaimer, the term of this patent is extended or adjusted under 35 U.S.C. 154(b) by 269 days.

(21) Appl. No.: 17/030,015

(22) Filed: Sep. 23, 2020

(65) Prior Publication Data

US 2022/0088297 A1 Mar. 24, 2022

(51) Int. Cl.
*A61M 5/165* (2006.01)
*A61M 5/142* (2006.01)
(Continued)

(52) U.S. Cl.
CPC .......... *A61M 5/165* (2013.01); *A61M 5/1424* (2013.01); *A61M 39/08* (2013.01); *A61M 39/10* (2013.01); *A61M 39/24* (2013.01); *A61M 2205/0216* (2013.01); *A61M 2205/7518* (2013.01); *A61M 2205/7554* (2013.01)

(58) Field of Classification Search
CPC .......... A61M 5/165; A61M 2005/1652–1657; A61M 2205/7527; A61M 5/38; A61M 2205/7554; B01D 19/0031
See application file for complete search history.

(56) References Cited

U.S. PATENT DOCUMENTS 2,664,085 A * 12/1953 Ryan .................... A61M 5/1411
604/252
2,704,544 A * 3/1955 Ryan .................... A61M 5/165
210/94
(Continued)

FOREIGN PATENT DOCUMENTS

CN 106474588 A 3/2017
GB 2077611 A * 12/1981 ............ A61M 5/165

OTHER PUBLICATIONS

International Search Report and Written Opinion for Application No. PCT/US2021/051358, dated Jan. 19, 2022, 19 pages.

*Primary Examiner* — Nathan R Price
*Assistant Examiner* — Anna E Goldberg-Richmeier
(74) *Attorney, Agent, or Firm* — Morgan, Lewis & Bockius LLP (57) ABSTRACT

IV filters are described herein. An IV filter includes a body, a filter media, and a bulb. The body defines a body volume. The filter media is disposed within the body volume. The filter media defines an inlet portion of the body volume and an outlet portion of the body volume. The filter media permits inlet flow from the inlet portion of the body volume to the outlet portion of the body volume and captures particulate from the inlet flow. The bulb defines a bulb volume in fluid communication with the outlet portion of the body volume. The bulb is deformable to compress the bulb volume and direct back flow from the outlet portion of the body volume through the filter media and into the inlet portion of the body volume, displacing particulate captured in the filter media into the inlet portion of the body volume.

17 Claims, 5 Drawing Sheets

(51) Int. Cl.
*A61M 39/08* (2006.01)
*A61M 39/10* (2006.01)
*A61M 39/24* (2006.01)

(56) References Cited

U.S. PATENT DOCUMENTS

| | | | | |
|---|---|---|---|---|
| 2,776,055 | A | * | 1/1957 | Myron .................. A61M 5/165 |
| | | | | 210/415 |
| 3,593,854 | A | | 7/1971 | Swank |
| 4,030,495 | A | * | 6/1977 | Virag .................... A61M 39/24 |
| | | | | 604/152 |
| 4,188,948 | A | * | 2/1980 | Swinton ............. B01D 19/0031 |
| | | | | 96/219 |
| 2010/0270222 | A1 | | 10/2010 | Lauer |

* cited by examiner

INTRAVENOUS FILTER

FIELD OF THE INVENTION

The present disclosure generally relates to filters, and, in particular, to filters for intravenous sets.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. During operation, medical fluid can be filtered to prevent the transfer of bacteria, microorganisms, and/or other pathogens.

In some applications, filters can become clogged, limiting the filtration efficiency and life of the filter.

SUMMARY

The disclosed subject matter relates to IV filters. In certain embodiments, an IV filter is disclosed that comprises a body defining a body volume; a filter media disposed within the body volume, the filter media defining an inlet portion of the body volume and an outlet portion of the body volume, wherein the filter media permits inlet flow from the inlet portion of the body volume to the outlet portion of the body volume and captures particulate from the inlet flow; and a bulb defining a bulb volume in fluid communication with the outlet portion of the body volume, wherein the bulb is deformable to compress the bulb volume and direct back flow from the outlet portion of the body volume through the filter media and into the inlet portion of the body volume, displacing particulate captured in the filter media into the inlet portion of the body volume.

In certain embodiments, a method is disclosed that comprises permitting an inlet flow from an inlet portion of a body volume through a filter media and into an outlet portion of a body volume; capturing particulate from the inlet flow in the filter media; directing a back flow from the outlet portion of the body volume through the filter media and into the inlet portion of the body volume; and displacing particulate captured in the filter media into the inlet portion of the body volume.

In certain embodiments, an IV set is disclosed that comprises a first portion of tubing; a second portion of tubing; and an IV filter comprising: a body defining a body volume; an inlet coupled to the first portion of tubing, wherein the inlet is in fluid communication with the body volume; an outlet coupled to the second portion of tubing, wherein the outlet is in fluid communication with the body volume; a filter media disposed within the body volume, the filter media defining an inlet portion of the body volume in fluid communication with the inlet and an outlet portion of the body volume in fluid communication with the outlet, wherein the filter media captures particulate from a flow from the inlet to the outlet; and a bulb defining a bulb volume in fluid communication with the outlet portion of the body volume, wherein the bulb is deformable to compress the bulb volume and direct back flow from the outlet portion of the body volume through the filter media and into the inlet portion of the body volume, displacing particulate captured in the filter media into the inlet portion of the body volume.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed IV filter incorporates a bulb in fluid communication with the body volume. The bulb can be deformable to direct back flow through the filter media, allowing particulate embedded in the filter media to be displaced. By displacing embedded particulate from the filter media, the life of the IV filter can be extended without reducing filtration efficiency.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the filters for the administration of medical fluid using the disclosed IV filter, it is to be understood that this description is only an example of usage and does not limit the scope of the claims. Various aspects of the disclosed filter may be used in any application where it is desirable to provide extended filter life without reducing filtration efficiency.

The disclosed connector overcomes several challenges discovered with respect to certain conventional filters. One challenge with certain conventional filters is that certain conventional filters can become clogged, limiting the filtering efficiency of the filter. For example, many treatments can utilize lipids or other large molecule components, which may clog filters in a short period of time. Because certain conventional filters may rapidly clog during the administration of treatments that utilize lipids or other large molecule components, and because clogged filters can interrupt the administration of medical fluids and require frequent replacement, the use of certain conventional filters is undesirable.

Therefore, in accordance with the present disclosure, it is advantageous to provide an IV filter as described herein that allows for embedded particles to be dislodged from the filter media, extending the life of the filter. Further, it is advantageous to provide an IV filter as described herein that allows for extended filtration life without reducing the filtration efficiency of the IV filter.

Examples of IV filters that allow for embedded particles to be dislodged are now described.

Figure 1:
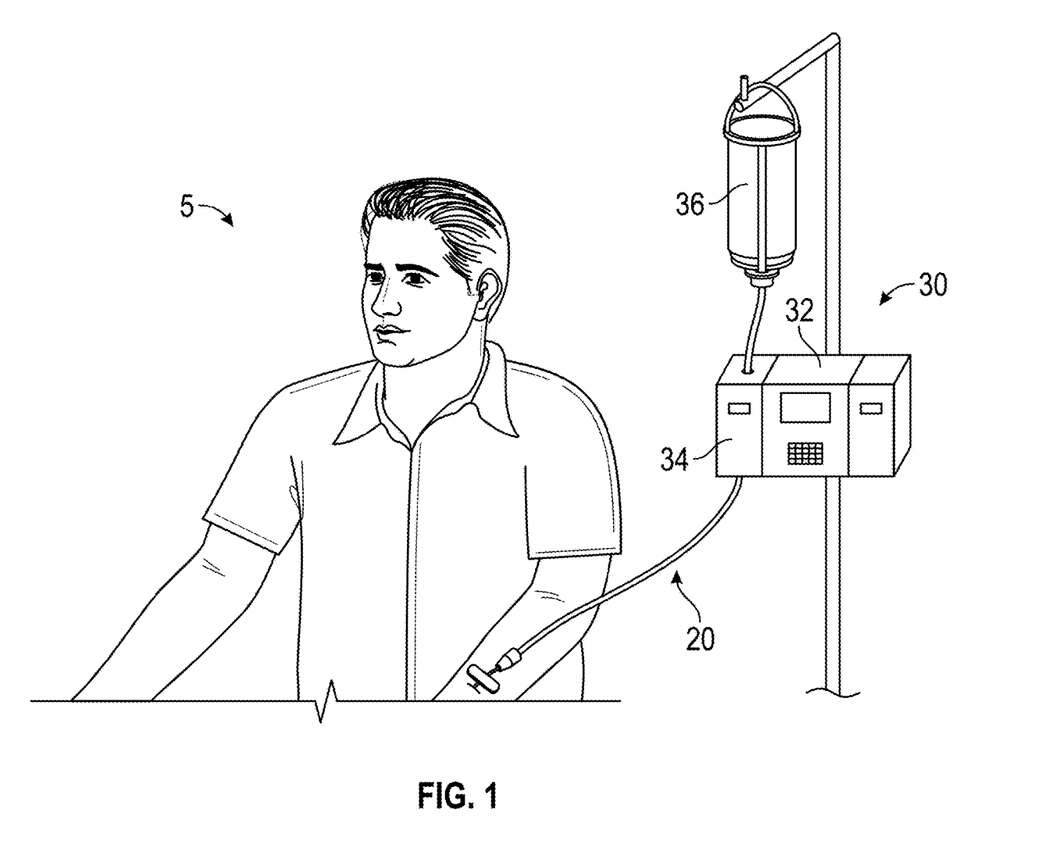
FIG. 1 illustrates a patient receiving an infusion of a medical fluid through an IV pump according to certain aspects of the present disclosure.

FIG. 1 illustrates a patient 5 receiving an infusion of a medical fluid through an IV pump 30 according to certain aspects of the present disclosure. The IV pump 30 comprises a controller 32 and two pump modules 34. An IV set 20 is connected between a container 36 of the medical fluid and the patient 5. During operation, medical fluid delivered to the patient 5 can be filtered to prevent the transfer of bacteria, microorganisms, and/or other pathogens. In some embodiments, an IV filter can be disposed in between or in line with tubing of the IV set 20.

Figure 2:
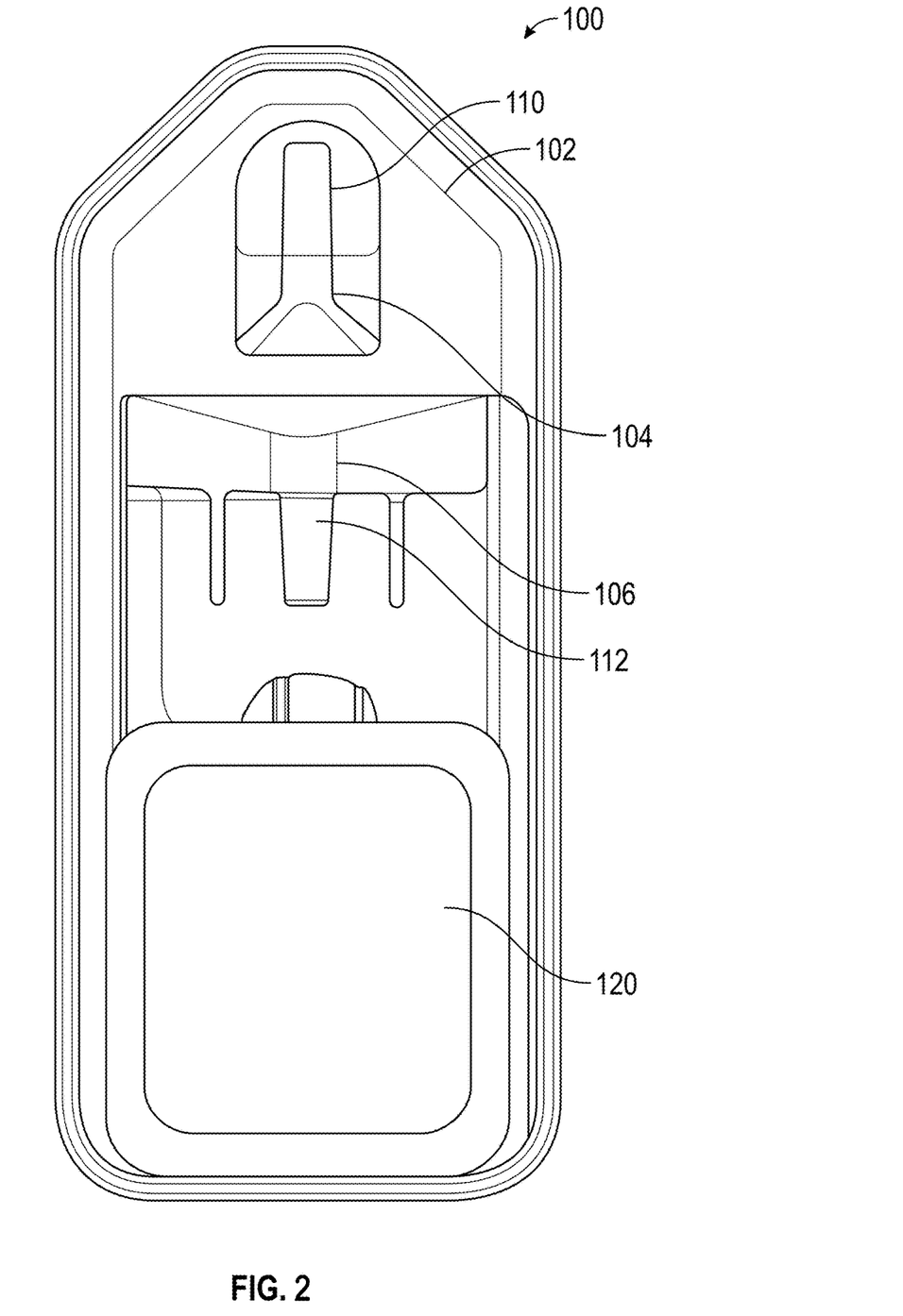
FIG. 2 illustrates a front view of the in-line IV filter according to certain aspects of the present disclosure.
Figure 3:
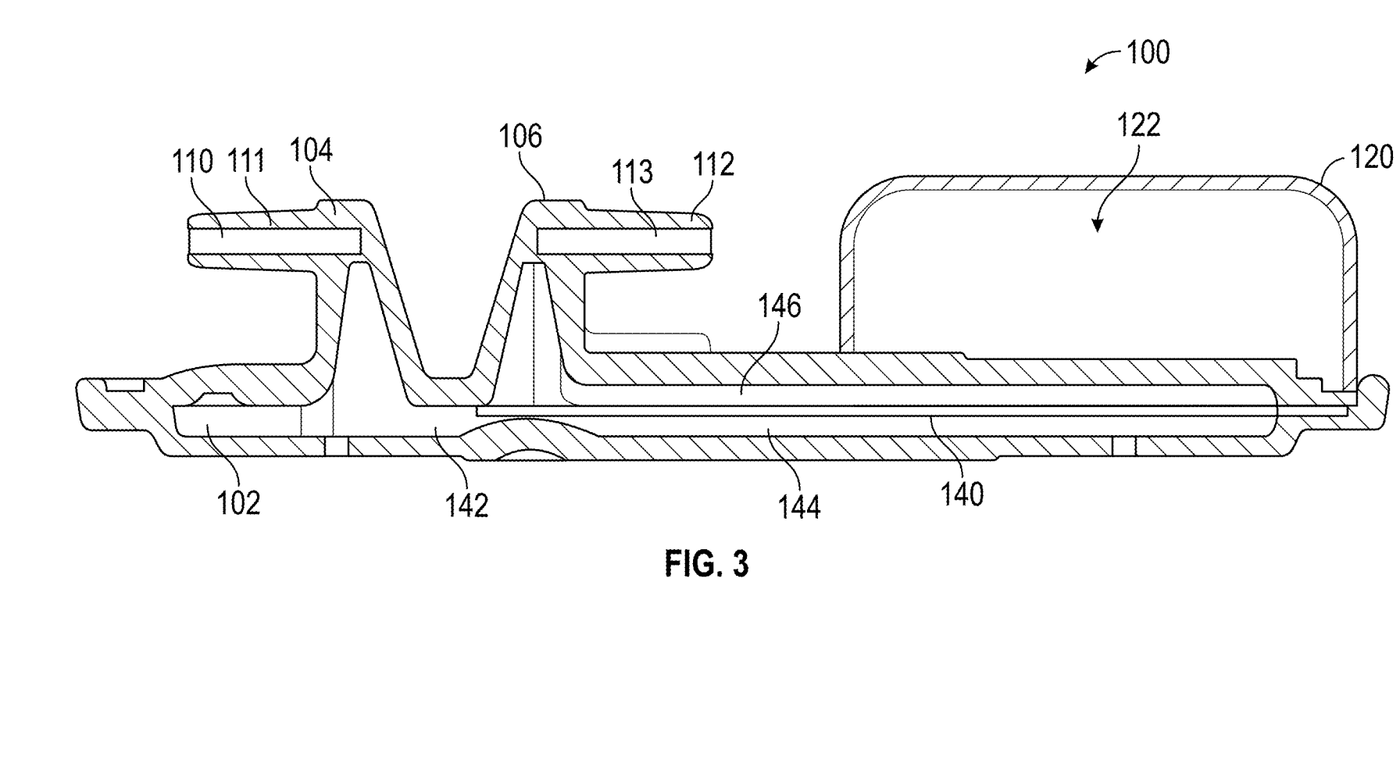
FIG. 3 illustrates a cross-sectional view of the in-line IV filter of FIG. 2.

FIG. 2 illustrates a front view of the in-line IV filter 100 according to certain aspects of the present disclosure. FIG. 3 illustrates a cross-sectional view of the in-line IV filter 100 of FIG. 2. With reference to FIGS. 2 and 3, the in-line IV filter 100 allows for filtration of fluids through an IV set.

In the depicted example, fluid flow enters the in-line IV filter 100 through an inlet 110 formed in a body 102 of the in-line IV filter 100. An inlet body 104 can extend away from the body 102 to define a protrusion forming the inlet 110. An inlet lumen 111 defined in the inlet body 104 provides fluid communication with a volume 142 defined within the body 102, permitting fluid flow to enter the in-line IV filter 100. The body 102 can be formed from a rigid material, including, but not limited to plastic.

In some embodiments, tubing from the IV set 20 can be coupled to the inlet 110 to allow flow from a fluid container 36 or other component of the IV set 20 into the volume 142 defined within the body 102. The fluid flow can have a positive pressure to pass through the in-line IV filter 100.

As illustrated, fluid within the volume 142 can pass through a filter media 140 to prevent the transfer of bacteria, microorganisms, and/or other pathogens to the patient. During operation, fluid can flow from an inlet portion 144 of the volume 142 through the filter media 140 to the outlet portion 146 of the volume 142. As can be appreciated, a positive pressure differential can direct fluid flow from the inlet portion 144 of the volume through the filter media 140 to the outlet portion 146 of the volume 142.

As described herein, the filter media 140 can selectively filter the flow through the in-line IV filter 100. The filter media 140 can have an average filter opening of approximately 0.2 micros. Optionally, the average filter opening of the filter media can range between 0.1 microns and 10 microns. In some embodiments, the filter media 140 can be formed from a non-woven filter material. The filter media 140 can be formed from a resilient or expandable material.

The filter media 140 can have a generally planar or rectangular prism shape. As illustrated, the filter media 140 can extend along a portion of the width and length of the body 102. In some embodiments, the filter media 140 can extend generally along the width of the body 102. During operation, fluid flow can flow into the filter media 140 along the surface area of the filter media 140 exposed to the inlet portion 144 of the volume 142.

As illustrated, the filter media 140 can be supported by portions of the body 102. In some embodiments, a lower portion of the filter media 140 can be captured between opposing portions of the body 102. Optionally, protrusions formed in the body 102 can further retain or support the filter media 140 within the volume 142. As illustrated, one or more protrusions formed in the body 102 can retain an upper portion of the filter media 140 within the body 102.

After passing through the filter media 140, the fluid flow can enter the outlet portion 146 of the volume 142. Outlet flow can exit the in-line IV filter 100 through an outlet 112 formed in a body 102 of the in-line IV filter 100. An outlet body 106 can extend away from the body 102 to define a protrusion forming the outlet 112. An outlet lumen 113 defined in the outlet body 106 provides fluid communication with a volume 142 defined within the body 102, permitting fluid flow to exit the in-line IV filter 100.

Similar to the inlet 110, in some embodiments, tubing from the IV set 20 can be coupled to the outlet 112 to allow flow from the volume 142 to the patient or other components of the IV set 20.

During operation, the inlet side of the filter media 140 can become clogged with particulate, limiting the filtering efficiency of the filter media 140. In some applications, treatments that utilize lipids or other large molecules can clog and reduce the filtering efficiency of the filter media 140 in a short period of time. As described herein, conventional filters are typically replaced when clogged with particulate.

Advantageously, the in-line IV filter 100 can dislodge sediment or particulate embedded in the filter media 140, extending the life of the in-line IV filter 100 without reducing filtration efficiency. As described herein, the in-line IV filter 100 can direct back flow or back pressure through the filter media 140 to dislodge particulate embedded in the inlet side of the filter media 140.

During a dislodging operation, back flow can be forced from the outlet portion 146 of the volume 142 through the filter media 140 to the inlet portion 144 of the volume 142. As can be appreciated, the dislodging operation can create a pressure differential across the outlet portion 146 and the inlet portion 144 of the volume 142. Dislodged particulate from the inlet side of the filter media 140 can flow into the inlet portion 144 of the volume 142. In some applications, the dislodged particulate can settle at a lower or bottom portion of the volume 142 to allow fluid flow through the filter media 140 without clogging.

In the depicted example, a clinician can actuate a bulb 120 to create back flow through the filter media 140. In some embodiments, the bulb 120 is formed from a resilient or deformable material that allows the bulb volume 122 defined by the bulb 120 to be reduced upon actuation. As illustrated, the bulb volume 122 is in fluid communication with the outlet portion 146 of the volume 142. The bulb 120 can be formed from any resilient or deformable material, including, but not limited to silicone, rubber, or thermoplastic elastomers. The bulb 120 can have a generally rectangular prism shape.

By reducing the bulb volume 122, the fluid within the bulb volume 122 and the outlet portion 146 of the volume 142 is pressurized relative to the fluid within the inlet portion 144 of the volume 142. Therefore, upon actuation or compression of the bulb 120, back flow is forced from the outlet portion 146 of the volume 142 through the filter media 140 to the inlet portion 144 of the volume 142, displacing or dislodging particulate from the inlet side of the filter media 140.

Prior to a dislodging operation, IV flow into the in-line IV filter 100 via the inlet 110 and flow out of the in-line IV filter 100 via the outlet 112 can be restricted or blocked to prevent back flow from entering the IV set 20. In some embodiments, the tubing coupled to the inlet 110 and/or the outlet 112 can be clamped to prevent inadvertent flow during the dislodging operation.

Figure 4:
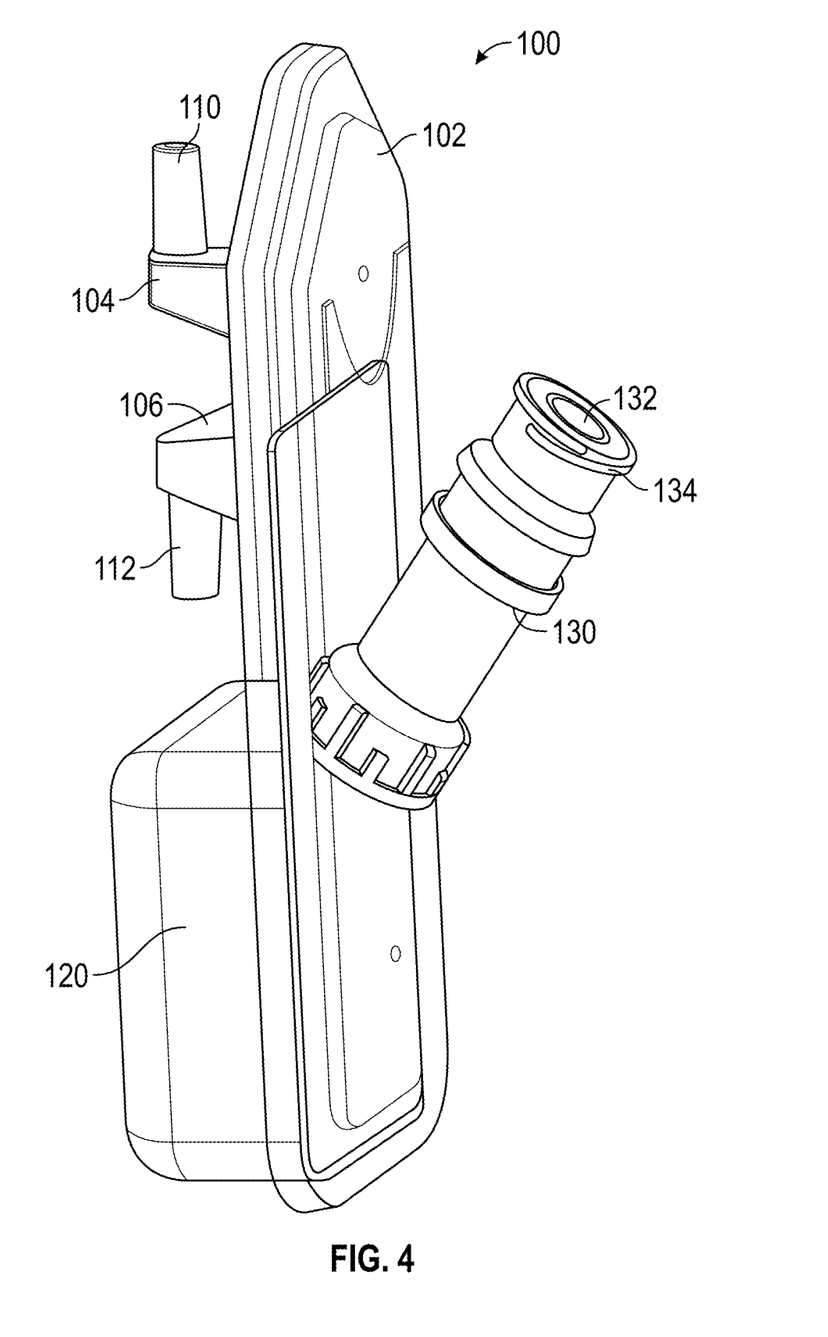
FIG. 4 illustrates a perspective view of an in-line IV filter according to certain aspects of the present disclosure.
Figure 5:
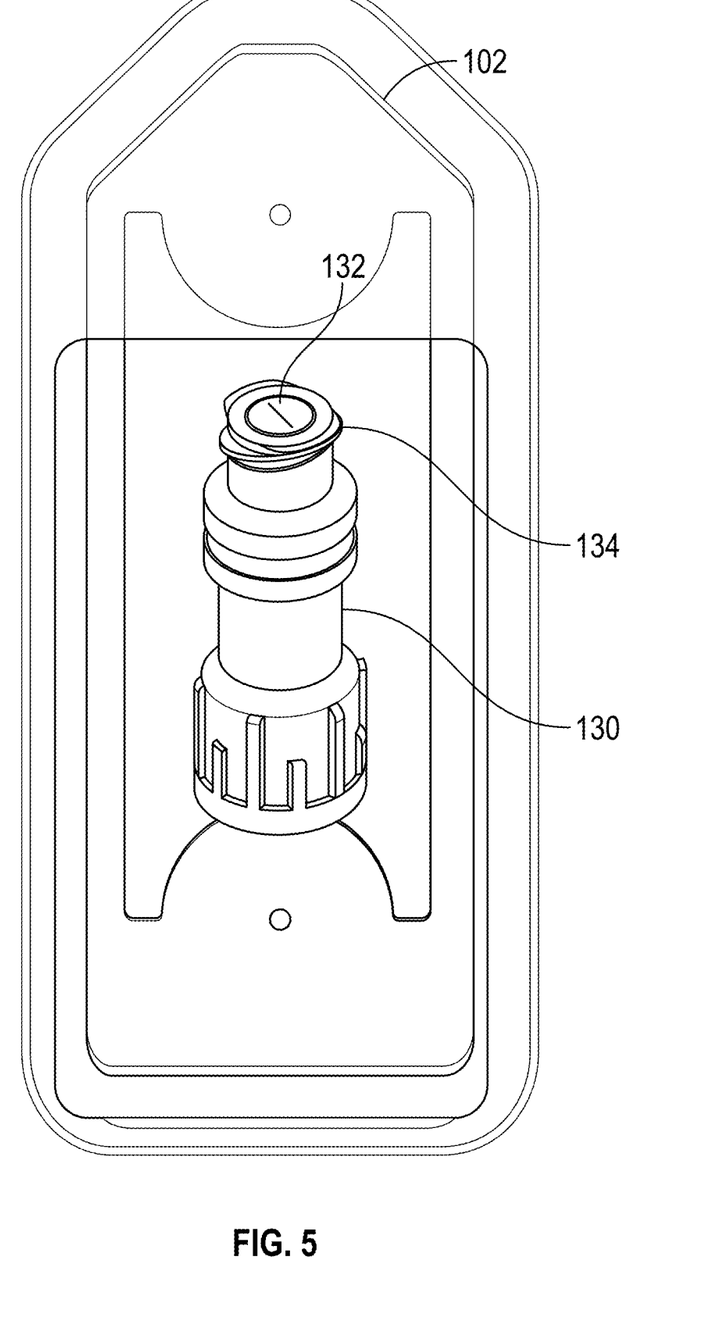
FIG. 5 illustrates a rear view of the in-line IV filter of FIG. 4.

FIG. 4 illustrates a perspective view of an in-line IV filter 100 according to certain aspects of the present disclosure. FIG. 5 illustrates a rear view of the in-line IV filter 100 of FIG. 4. In some embodiments, the in-line IV filter 100 can include an aspiration valve 130 to allow particulate dislodged from the filter media 140 to be removed from the inlet portion 144 of the volume 142. Advantageously, by removing particulate from the in-line IV filter 100, the useful life of the in-line IV filter 100 can be further extended without reducing filtration efficiency.

In the depicted example, the aspiration valve 130 is in fluid communication with the inlet portion 144 of the volume 142. Optionally, the aspiration valve 130 is in fluid communication with a lower portion of the inlet portion 144 of the volume 142 where dislodged particulate is expected to settle. A clinician can attach or couple a syringe to the port 132 and/or connector body 134 of the aspiration valve 130. The syringe can draw out displaced particulate through the port 132 of the aspiration valve 130. In some embodiments, the aspiration valve 130 is a needleless connector.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An IV filter, comprising:
   a body defining a body volume;
   a filter media disposed within the body volume, the filter media defining an inlet portion of the body volume and an outlet portion of the body volume, wherein the filter media permits inlet flow from the inlet portion of the body volume to the outlet portion of the body volume and captures particulate from the inlet flow;
   a bulb defining a bulb volume in fluid communication with the outlet portion of the body volume, wherein the bulb is deformable to compress the bulb volume and direct back flow from the outlet portion of the body volume through the filter media and into the inlet portion of the body volume, displacing particulate captured in the filter media into the inlet portion of the body volume; and
   an aspiration valve in selective fluid communication with a lower portion of the inlet portion of the body volume, wherein the aspiration valve is configured to remove displaced particulate within the inlet portion of the body volume.

2. The IV filter of claim 1, wherein the aspiration valve comprises a needleless connector.

3. The IV filter of claim 1, further comprising an inlet in fluid communication with the inlet portion of the body volume.

4. The IV filter of claim 3, further comprising an outlet in fluid communication with the outlet portion of the body volume.

5. The IV filter of claim 4, wherein the inlet is in fluid communication with the outlet through the filter media.

6. The IV filter of claim 1, wherein the bulb comprises a resilient material.

7. The IV filter of claim 1, wherein the bulb comprises silicone, rubber, or thermoplastic elastomer.

8. The IV filter of claim 1, wherein the bulb comprises a rectangular prism shape.

9. A method comprising:
   permitting an inlet flow from an inlet portion of a body volume through a filter media and into an outlet portion of the body volume;
   capturing particulate from the inlet flow in the filter media;
   directing a back flow from the outlet portion of the body volume through the filter media and into the inlet portion of the body volume;
   displacing particulate captured in the filter media into the inlet portion of the body volume; and
   removing the particulate from the inlet portion of the body volume.

10. The method of claim 9, further comprising:
    compressing a bulb volume to direct the back flow from the outlet portion of the body volume through the filter media and into the inlet portion of the body volume.

11. The method of claim 10, further comprising:
    deforming a bulb to compress the bulb volume.

12. The method of claim 9, further comprising:
    preventing flow through an inlet and an outlet during the directing the back flow from the outlet portion of the body volume through the filter media and into the inlet portion of the body volume.

13. An IV set, comprising:
    a first portion of tubing;
    a second portion of tubing; and
    an IV filter comprising:
      a body defining a body volume;
      an inlet coupled to the first portion of tubing, wherein the inlet is in fluid communication with the body volume;
      an outlet coupled to the second portion of tubing, wherein the outlet is in fluid communication with the body volume;
      a filter media disposed within the body volume, the filter media defining an inlet portion of the body volume in fluid communication with the inlet and an outlet portion of the body volume in fluid communication with the outlet, wherein the filter media captures particulate from a flow from the inlet to the outlet;
      a bulb defining a bulb volume in fluid communication with the outlet portion of the body volume, wherein the bulb is deformable to compress the bulb volume and direct back flow from the outlet portion of the body volume through the filter media and into the inlet portion of the body volume, displacing particulate captured in the filter media into the inlet portion of the body volume; and
      an aspiration valve in selective fluid communication with a lower portion of the inlet portion of the body volume, wherein the aspiration valve is configured to remove displaced particulate within the inlet portion of the body volume.

14. The IV set of claim 13, further comprising one or more valves to prevent back flow through the first portion of tubing or the second portion of tubing.

15. The IV set of claim 13, wherein the aspiration valve comprises a needleless connector.

16. The IV set of claim 13, wherein the bulb comprises a resilient material.

17. The IV set of claim 13, wherein the bulb comprises silicone, rubber, or thermoplastic elastomer.

* * * * *